United States Patent [19]

Renon et al.

[11] 4,393,689
[45] Jul. 19, 1983

[54] DEVICE FOR DETERMINING PHYSICAL CHARACTERISTICS OF A FLUID, SUCH AS ITS LIQUID-VAPOR EQUILIBRIUM PRESSURE

[75] Inventors: Henri Renon, Paris; Dominique Richon, Aulnay-sous-Bois, both of France

[73] Assignees: Institut Francais du Petrole, Rueil-Malmaison; Association pour la Recherche et le Developpment, Paris, both of France

[21] Appl. No.: 254,722

[22] Filed: Apr. 16, 1981

[30] Foreign Application Priority Data

Apr. 16, 1980 [FR] France .............................. 80 08568

[51] Int. Cl.³ ............................................. G01N 7/14
[52] U.S. Cl. ..................................................... 73/64.2
[58] Field of Search ..................................... 73/64.2, 29

[56] References Cited

U.S. PATENT DOCUMENTS 3,528,440 9/1970 Plucker ............................ 73/64.2 X

FOREIGN PATENT DOCUMENTS 974183 11/1964 United Kingdom .

OTHER PUBLICATIONS

Gibbs, R. E., et al. *Vapor–Liquid Equilibria from Total-Pressure Measurements, A New Apparatus,* In Ind. Eng. Chem. Fund., vol. 11, No. 3, pp. 410–413, Aug. 1972.
Zel'venskii, Y. D., et al., *Apparatus for Studying Liquid–Vapor Equilibrium at High Pressures,* In Ind. Lab. vol. 38, No. 3, pp. 447–448, Mar. 1972.

*Primary Examiner*—James J. Gill
*Assistant Examiner*—Joseph W. Roskos
*Attorney, Agent, or Firm*—Millen & White

[57] ABSTRACT

This device comprises (a) a removable compact cell which can be accurately weighed. A sample is introduced into this cell, with the cell equipped with a magnetic stirrer and with at least one measuring gauge. This cell has a sliding cover plate for varying its volume. The device includes (b) a pressurizing unit whose temperature can be controlled and which is provided with a housing for receiving the cell. In combination with the above, there is provided (c) a calibrated hydraulic press operatively associated with the sliding cover plate to compress the fluid contained in the cell.

10 Claims, 8 Drawing Figures

DEVICE FOR DETERMINING PHYSICAL CHARACTERISTICS OF A FLUID, SUCH AS ITS LIQUID-VAPOR EQUILIBRIUM PRESSURE

BACKGROUND OF THE INVENTION

The present invention relates to a device for determining the physical characteristics of a fluid comprising a vapor phase, such as its liquid-vapor equilibrium pressure.

Knowing the liquid-vapor equilibrium of fluid mixtures is of great importance in certain techniques, such as in operations of separation by distillation and adsorption, in the exploitation of oil or natural gas deposits, in techniques of refrigeration or production of thermal energy by heat pumps which make use of liquid vaporization or vapor absorption in a suitable solvent under determined temperature and pressure conditions.

It is possible to carry out measurements on a fluid by placing it in a chamber where it can be compressed.

To obtain a sufficient accuracy in the preformed measurements, it is however necessary to solve the difficult problems of introduction of the fluid under study into the chamber and of temperature regulation, with the additional problem of compatability between the fluid under study, and mercury when the latter is used to apply compression to the fluid.

An apparatus for measuring vapor pressure is described in French Pat. No. 1,396,489.

However, this apparatus permits neither stirring and weighing of the sample, nor accurate determinations of its composition.

Furthermore, it suffers from the drawback of leaving an large dead volume around the bellow and does not permit uniform thermoregulation.

British Pat. No. 974,103 describes an apparatus for measuring quantities of dissolved gas, which is not suitable for accurately determining liquid molar fractions.

The shape of the cell of this apparatus is moreover, complex and makes thermoregulation difficult. This British patent does not make provision for accurate measurement of liquid densities.

Furthermore, this prior art device requires the use of models for processing data relating to pressure values.

The publication of GIBBS and VAN NESS in Industrial and Engineering Chemistry Fundamentals (11,410,1972) describes an apparatus of constant volume which can only be used for liquid-vapor equilibrium measurements. The molar fractions in liquid phase are, however, derived from a model and not from direct sample weighing. It is difficult to estimate the vaporized fraction particularly at high pressures (the results given by the authors are relative to pressures lower than one atmosphere). The introduction of the compounds under study is effected by means of volumetric pumps, and requires knowledge of the fluid density at the inlet pressure, in order to determine the fluid masses introduced into the cell.

SUMMARY OF THE INVENTION

The drawbacks of these prior art devices are obviated with the device according to the invention which is described below with more particular reference, by way of non limitative example, to its application in the study of liquid-vapor mixtures in the vicinity of their bubble point pressure at a given temperature.

This device comprises an equilibrium cell designed to permit very accurate weighing of the introduced compounds, and a uniform, complete thermostating of the system. The device makes it also possible, due to an associated hydraulic press system, to completely eliminate the vapor phase from the cell so that the bubble point pressure at the studied temperature can be determined without requiring the corrections necessitated by the presence of a vapor phase.

BRIEF DESCRIPTION OF THE DRAWINGS

An embodiment of the invention is illustrated by the accompanying drawings, wherein.

DETAILED DISCUSSION OF THE INVENTION

Figure 1A:
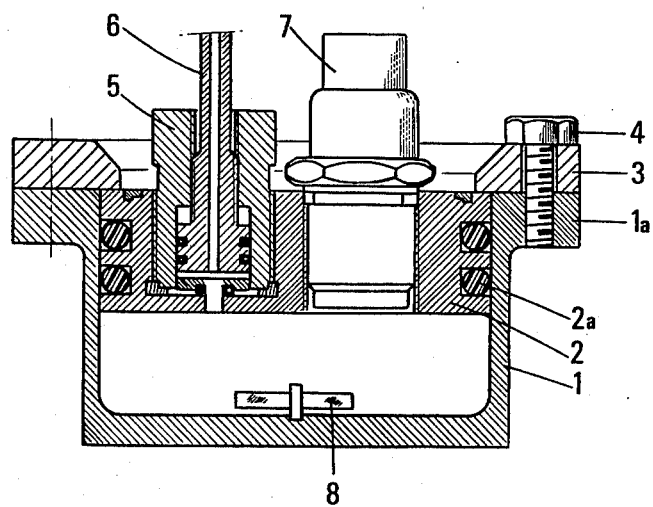
FIGS. 1 and 1A illustrate the cell of variable volume of this device, as seen from above in FIG. 1 and in axial cross-section along line AA of FIG. 1, FIGS. 2 and 2A show respectively FIG. 1A in the same cell of FIGS. 1 and 1A equipped with means for holding its cover plate in upper position.
Figure 1:
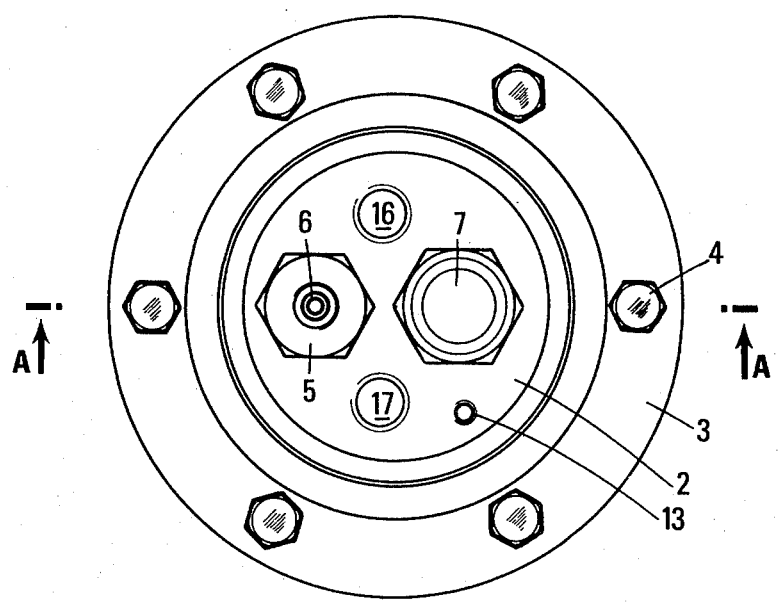

FIGS. 1 and 1A illustrate an embodiment of the measuring cell.

Reference 1 designates the body of the cell. The latter is closed with a cover plate 2 which forms a moveable wall slidably mounted in the cell, thus permitting variation of the volume of the housed fluid by compression thereof.

O-rings 2a positioned around the cover plate 2 provide for the sealing between the interior and the exterior of the cell.

The cell presents at its upper part a flange 1a to which is adapted a collar 3 secured to this flange such as by screws 4, this collar preventing the cover plate 2 from escaping under the action of the pressure prevailing inside the cell when the latter is located outside the pressurizing unit 10.

The cell is provided with means for introducing the fluid, comprising in this embodiment a loading valve 5 carried by the cover plate 2 controlling the introduction of gaseous products into the cell.

The cell is also provided with one or more measuring gauges or sensors which comprise at least one pressure sensor 7 adapted to the cover plate 2 and enabling the evolution of the pressure within the cell to be followed, and a temperature sensor(located in a housing indicated by the reference 13 as shown in FIG. 1).

The pressure sensor 7, which may be of a known type is connected to displaying means via electrical conductor (not shown).

The cell also comprises means for homogenizing and stirring the phases contained in this cell, these means comprising, for example, the bar magnet 8.

The cell 1, of compact shape, is made of a sufficient light material to enable the assembly of the cell 1, the cover plate 2, the valve 5 and the sensor 7 to be weighed on precision scales.

This cell will advantageously be made of titanium which is a light metal and enables stirring of the mixture contained in the cell to be effected by means of a magnetic stirrer 9 positioned under the bottom of the pressurizing unit 10 (FIG. 2) which is, for example, made of stainless steel.

The mouthpiece 6 of the loading valve may at will be connected to a device for creating a vacuum within the cell 1, or to a source of the product under study.

Figure 2A:
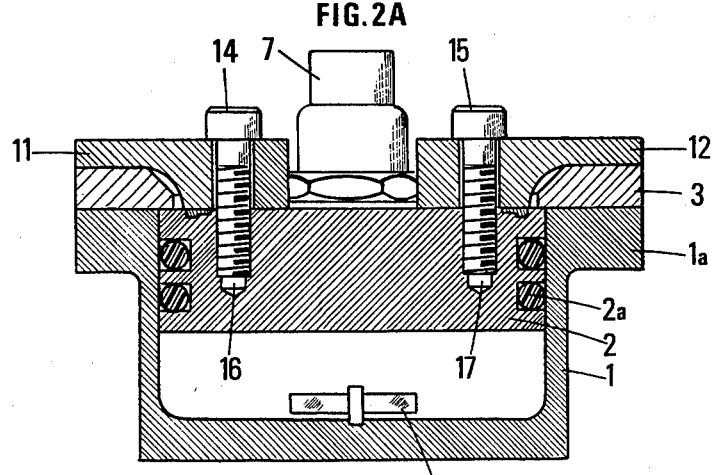
Figure 2:
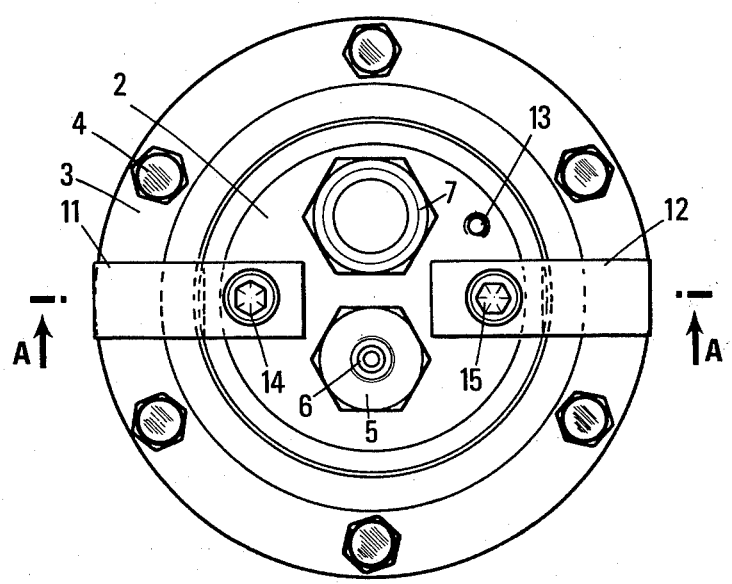

In order to prevent the cover plate 2 from sliding downwardly in the cell 1 when a vacuum is created in this cell prior to loading thereof, means for holding this cover plate in upper position can be adapted to the collar 1a, these means comprising, for example, two supporting lugs 11 and 12 resting on the collar 3, these supporting lugs 11 and 12 carrying securing screws 14 and 15 screwed on corresponding threadings 16 and 17 provided at the upper part of the cover plate 2 (FIGS. 2 and 2A).

The elements 11, 12, 14 and 15 may be disassembled after the cell has been filled with the products.

Figure 3:
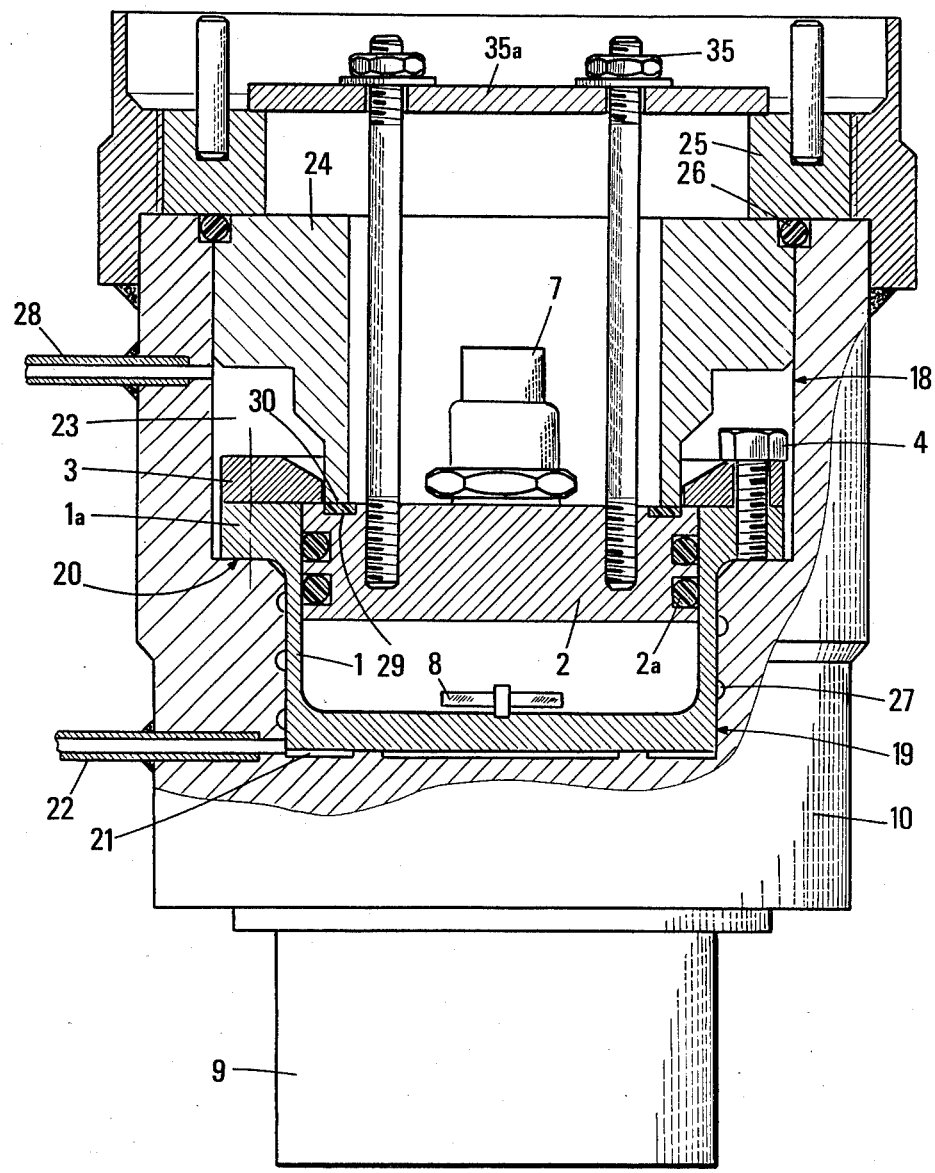
FIG. 3 is an axial cross-section of the cell positioned in the pressurizing unit, FIGS. 4A and 4B diagrammatically show the assembly of the device, respectively before and after compression of the fluid under study, and FIG. 5 diagrammatically shows a device for loading the cell with gas.

FIG. 3 shows the cell 1 positioned within the pressurizing unit 10, above the magnetic stirrer 9.

A cylindrical recess 18 opens at the upper part of the pressurizing unit 10, this recess having an internal diameter greater than the diameter of the flange 1a of the cell 1, and than that of the collar 3. Within the unit 10, the recess 18 is connected, and in communication with a cylindrical bore 19 which can house the cell 1, and whose internal diameter is substantially equal to the external diameter of the cell 1, with the provision of a small clearance, so that the cell can slide in the bore 19.

A cylindrical shoulder 20 separates the bore 19 from the recess 18.

The distance between this shoulder and the bottom of the bore 19, is such that the shoulder 20 constitutes a holding abutment for the flange 1a when the cell is moved into the bore 19, leaving a residual space, or first chamber 21, for the admission of pressurized hydraulic fluid through an inlet pipe 22 which opens into this chamber 21.

A second chamber 23 is provided above the collar 3 in the recess 18, and is defined between the internal wall of this recess 18 and the external wall of an annular element 24 secured by a threaded ring 25 at its upper part.

An annular gasket 26 provides for sealing between the holding element 24 and the internal wall of the recess 18 of the pressurizing block 10.

Through a helical groove 27 provided in the wall of the bore 19, the pressurized hydraulic fluid can flow from the chamber 21, into the chamber 23.

The latter is provided with a return pipe 28.

The upper face of the cover plate 2 of the measuring cell is adapted to be sealingly pressed against the lower end 30 of the holding element 24. To this end a flat sealing gasket 29, housed in an annular groove provided in the upper face of the cover 2, is pressed against the lower rim 30 of the holding element 24 by tightening screws 35 (FIG. 3) which are screwed in the bores 16 and 17 of the cover plate 2, these screws bearing on a clamping member 35a positioned on the ring 25.

Under these conditions, admission of pressurized hydraulic fluid into the chamber 21 causes upward displacement of the cell in the pressurizing unit 10, since this fluid is prevented from flowing out through the pipe 28. The cover plate 2 itself remains stationary, being held in position by the holding element 24, and consequently the internal volume of the cell decreases, thereby compressing the fluid contained in this cell.

The sliding cover plate 2 prevents any contact between the fluid contained in the cell 1 and the hydraulic fluid used for the compression.

Figure 4A:
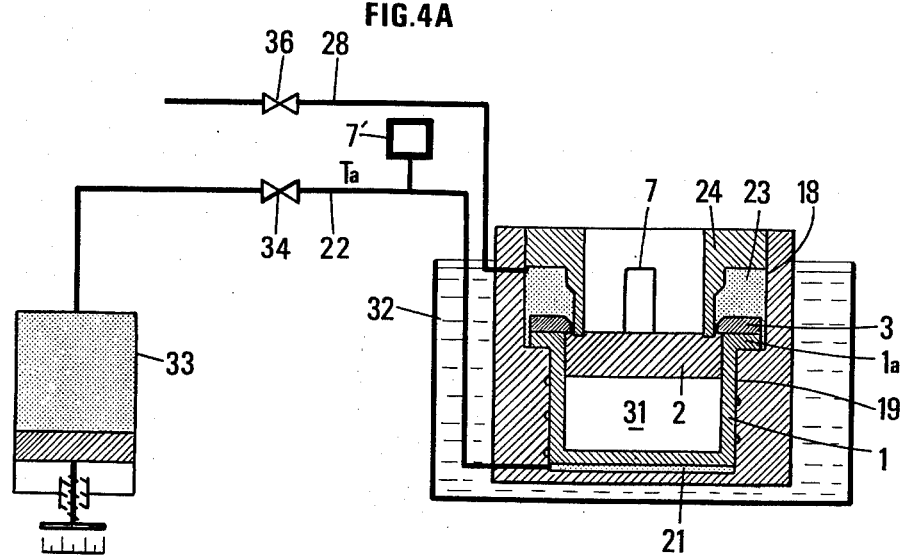
Figure 4B:
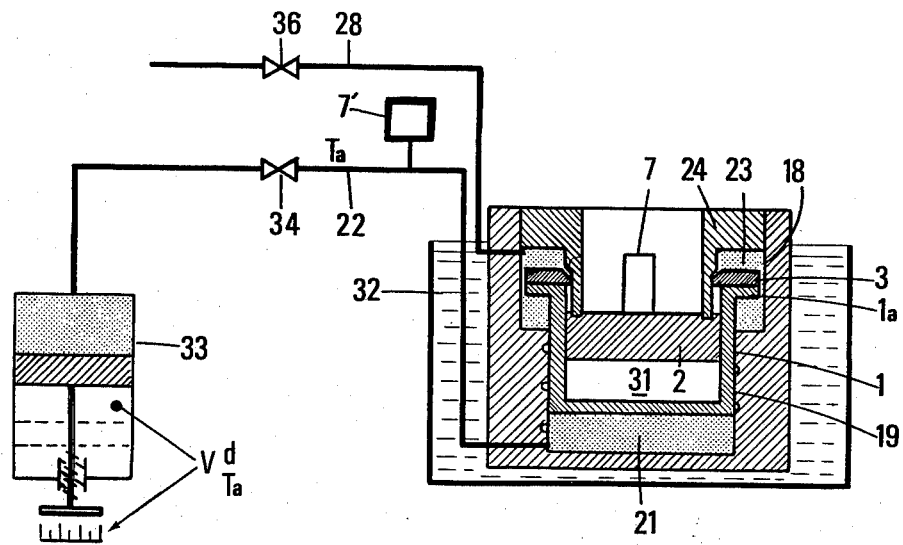

FIGS. 4A and 4B diagrammatically represent the assembly of the device according to the invention respectively before and after compression of the fluid 31 which is placed in the measuring cell 1.

The pressurizing unit 10 is positioned in a thermostatic bath 32 (the thermostat may be of a known type), whose temperature is maintained at a given value $T_f$.

The maximum volume of the cell 1 may be determined by a preliminary calibration.

An oil of low compressibility may advantageously be used as pressurizing fluid (so that the applied pressure is transmitted as efficiently as possible), this oil having a small coefficient of thermal dilatation, having regard to the temperature difference $T_f - T_a$.

The experimental procedure to be followed for determining experimental data with a device according to the invention is described below.

I. CALIBRATIONS

1. Pressure sensors

The pressure sensor 7 located on the equilibrium cell 1 has been calibrated for the different temperatures of utilization by using a Bourdon tube gage.

A pressure sensor 7' connected with the pressurizing circuit has been calibrated at room temperature also with the help of a Bourdon tube gage.

2. Internal volume $V_{cc}$ of the equilibrium cell

An evaluation of this volume has been obtained by measuring at different temperatures the pressures corresponding to the introduction of certain nitrogen amounts into the equilibrium cell 1, the introduced nitrogen masses being measured by weighing with a precision of 1/10000 gram. The tables and charts (P,V,T) of the National Bureau of Standards, Cryogenic Division, Institute for Basic Standards, Boulder, Colo., 1973, were used for this purpose.

The various performed measurements have led to the value:

$$V_{cc} = 54.49 \pm 0.18 \text{ cm}^3$$

3. Calibration of the hydraulic press

This calibration was effected by weighing the quantity of pressurizing fluid displaced by one or several rotations of the actuating wheel of the press 33.

For each full rotation of this wheel the displaced volume, measured at room temperature and pressure was $$V_d{}^{Ta,Pa} = 0.972 \pm 0.008 \text{ cm}^3$$

II. LOADING OF THE CELL

The cell is first weighed after a vacuum has been created therein, the cover plate or piston 2 being held in position by the components 11, 12, 14, 15 of the means for securing this piston (FIG. 2). The mass $m_{ce}$ of the empty cell is thus determined.

1. Loading with a liquid product

The liquid is introduced into the cell by means of a syringe. After the cell 1 has been connected to the circuit of FIG. 5 through a connecting element, the liquid is degassed, the valves $V_1$, $V'_4$ and $V_5$ being closed and the valves $V_2$, $V_4$ and $V_6$ being open.

When degassing has been achieved, the valve 5 is closed and the cell is disconnected from the degassing circuit, and weighed again in order to determine the mass of the introduced liquid (by difference with the weight of the empty cell).

REMARK: Degassing may be effected in some cases by a cycle of freezing periods followed with periods during which a vacuum is created.

2. Loading of a gaseous product

Figure 5:
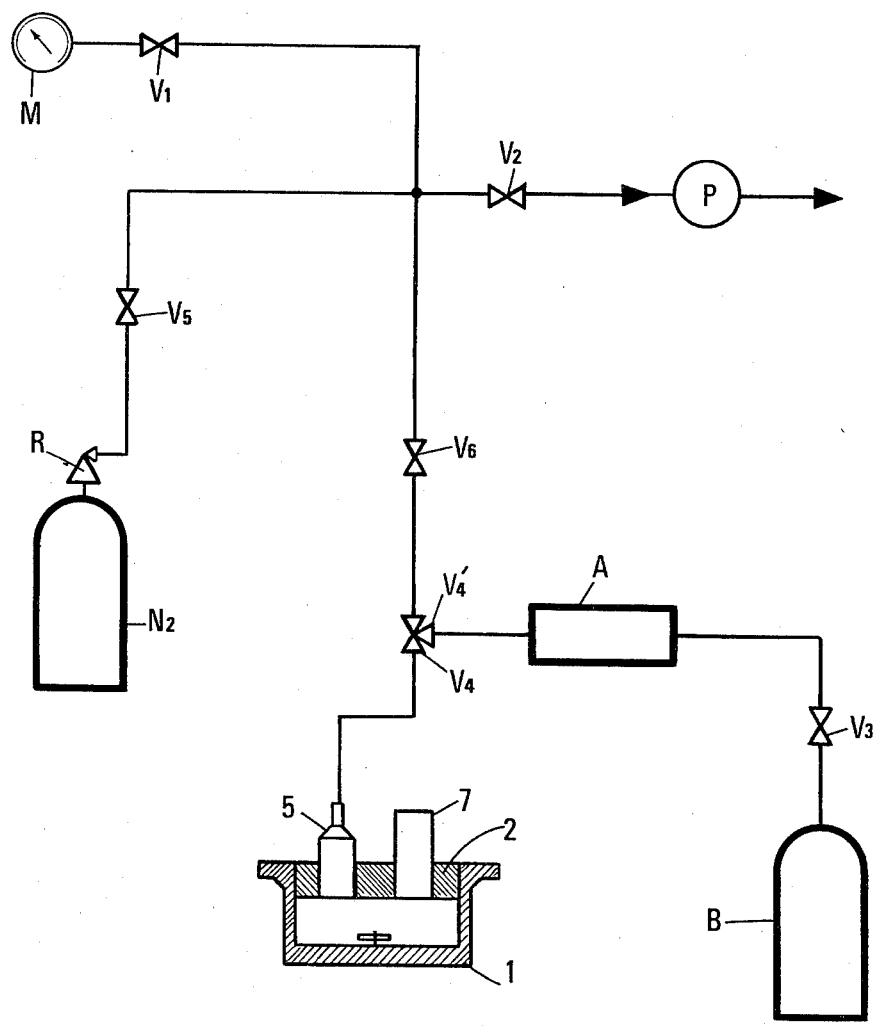

Taking into account the mass of the introduced liquid compound and the desired overall molar fraction for the mixture under study, an estimation is made of the number of moles of gaseous compounds to be introduced into the equilibrium cell. The cell is connected to the loading circuit (FIG. 5).

The valves $V_3$, $V_5$ and 5 being closed, and the valves $V_1$, $V_2$, $V_4$, $V'_4$ and $V_6$ being open, a vacuum is created in the circuit.

After closure of the valve $V_2$, the gaseous compound is introduced into the intermediary tank A of known volume, under a pressure which is read on the pressure gage M. The valve $V_3$ being closed, and the liquid in the cell 1 being frozen, the valve 5 is opened until the pressure indicated by the pressure gage M reaches the value corresponding to the desired pressure drop and thus to the number of moles of gaseous compound to be introduced into the cell 1.

Another weighing of the cell 1 makes it possible to ascertain the gas mass actually introduced into this cell and to determine the overall molar fraction of the prepared mixture.

REMARK: The remaining part of the gaseous component contained in the tank A may be kept in place in view of a subsequent loading of the cell by closing the valve $V'_4$.

3. Application to the preparation of an ethane (1)-n-do-decane (2) mixture having an overall ethane molar fraction z=0.75

The experimental results were the following:
Weight of the empty cell: $m_{ce} = 965.6186$ grams
Weight of the cell containing the dodecane $m_{ce}^D = 984.3370$ g.

This corresponds to a number of dodecane mole $n_2 = 0.1098$ in the cell 1.

About 0.33 mole of ethane is necessary to obtain an overall molar fraction of 0.75.

Ethane was then introduced into the tank A under a pressure of 35 bars, which corresponds to 0.41 mole.

Charts indicate that in order to obtain 0.33 mole of ethane, the pressure in the tank A must be lowered to 9.6 bars and this was accordingly effected.

Weighing gave $m_{ce}^{E+D} = 994.8025$ g, i.e., 0.3479 mole of ethane, and $z_1 = 0.7600$.

III. MEASURING THE BUBBLE POINT PRESSURE AND THE MOLAR VOLUME

The loaded cell 1 is placed into its pressurizing block 10 together with the different sealing elements. The assembly is then thermostated at the test temperature and the magnetic stirrer is actuated.

1. Loading of the pressurizing circuit

The degassed pressurizing fluid is introduced under vacuum into the press 33 (FIG. 4A).

The interior of the pressurizing unit 10 is put under vacuum by opening the valve 36, then the pressurizing fluid is injected into the block by means of the press 33 (FIG. 4B), the valve 34 being open; when the fluid reaches the level of the valve 36, the latter is closed.

By using a thermocouple housed in the piston of the cell, it is possible to know when the desired temperature is reached in the cell.

It is sufficient to compress with the pressurizing fluid until both pressure sensors 7 et 7' indicate the same value.

This will constitute the zero or start point for the compression of the mixture in the cell 1; from this moment the pressure curve of the mixture versus the displaced fluid volume $P = f(Vd)$ can be recorded. Disappearance of the vapor phase is accompanied by a discontinuity in the curve $P = f(Vd)_1$.

The corresponding angular point of the curve permits determination of the bubble point and computation of the molar volume of the mixture, after a correction which takes into account the compressibility coefficient B and the thermal dilatation coefficient $\alpha$ of the pressurizing fluid, as will be indicated in the following description of a particular application.

2. APPLICATION: Study of an ethane (1)-n-dodecane (2) mixture at 35° C. (composition $z_1 = 0.7600$)

The hydraulic press 33 has delivered a volume $V_d = 3.536$ cm$^3$ between the compression start at 36.3 bars and the time when the bubble point pressure $P_b = 37.8$ bars is reached (angular point of the curve $P = f(V)$).

The temperature correction is to be effected on the displaced volume, between 150° and 35° C., i.e., $$V_{d, T=35} = V_d \times (1 + \alpha \Delta T)$$
$$= 3.536 \times (1 + 1{,}134 \times 10^{-3} \times 20)$$
$$= 3616 \text{ cm}^3.$$

The correction required by the oil compressibility must be effected for the entire volume of the pressurizing fluid, i.e. the volume of the entire circuit less the volume displaced by the press to reach the pressure of the mixture, i.e., 96.4 cm$^3$.

$$\text{Correction for compressibility} = 96.4 \times \beta \times P$$
$$= 96.4 \times 0{,}111 \times 10^{-3} \times 1.5$$
$$= 0.016 \text{ cm}^3$$
$$\text{or } V = 0.016 \text{ cm}^3$$

The volume variation of the cell, $V_{var}$ is given by:

$$V_{var} = V_{d, T=5} - V$$
$$= 3.600 \text{ cm}^3$$

The volume $V_{mel}$ occupied by the mixture at the bubble point pressure, at the test temperature, is equal to the maximum volume of the cell less the volume variation $V_{var}$, i.e. $V_{mel} = 50.89$ cm$^3$.

The molar volume is given by the ratio of the volume mixture $V_{mel}$ to the total mole number in the mixture, i.e. $v = 0.1112$ liter/mole.

What is claimed is:

1. A device for determining physical characteristics of a fluid, such as its liquid-vapor equilibrium pressure or its volumetric mass, said device comprising in combination:

(a) a removable compact cell (1) adapted for being accurately weighed, said cell (1) comprising means (6) for introducing the fluid and means (8,9) for homogenizing and stirring the fluid contained therein, at least one measuring gauge (7), and said cell having a slidable wall (2);

(b) a pressurizing unit (10) adapted for having its temperature controlled, and provided with a housing (19) for receiving said removable cell (1); and (c) means for reducing the internal volume of said cell (1) comprising calibrated compression means (33) associated with said pressurizing unit (10) and operatively associated with said slidable wall (2) of said cell (1) for compressing the fluid contained therein.

2. A device according to claim 1, wherein cell (1) is made of titanium.

3. A device according to claim 1 wherein said homogenizing and stirring means comprise a magnetic stirrer (8,9).

4. A device according to claim 2 wherein said homogenizing and stirring means comprise a magnetic stirrer (8,9).

5. A device according to claims 1, 2, 3, or 4 wherein said cell (1) is adapted to fit in a housing (19) of complementary shape provided in said pressurizing unit (10), and wherein said means for reducing the volume of said cell further comprises a circuit (22) for admitting a pressurized hydraulic fluid into said housing (19) of the pressurizing unit (10).

6. A device according to claim 5, wherein said circuit for admitting a pressurized hydraulic fluid comprises press means (3) adapted for accurately measuring the volume of hydraulic fluid which is displaced during the compression of the fluid in said cell (1).

7. A device according to claim 5, wherein said cell (1) is slidably mounted in a piston like manner in said housing (19) of said pressurizing unit (10), and said slidable wall (2) comprises a slidable cover plate and wherein a chamber (21) for admitting pressurized fluid is defined between the bottom of said cell (1) and the bottom of said housing (19), with said pressurizing unit (10) comprising securing means (24) forming an abutment holding said sliding cover plate (2) when the bottom of the cell (1) is moved apart from the bottom of its housing (19) under the action of a hydraulic fluid pressure.

8. A device according to claim 7, wherein said measuring cell (1) is provided with a flange (1a) cooperating with means (3) for preventing said sliding cover plate (2) from escaping under the action of a pressure within the cell (1), a recess (18) of a diameter greater than that of said flange (1a) opening in said pressurizing unit (10), said recess (18) being connected to said housing (19) of said cell (1) through a shoulder (20) which defines a holding abutment for said cell (1) and provides between the bottom of this cell (1) and the bottom of said housing (19) a residual space (21) constituting said chamber for admitting pressurized fluid, said securing means comprising a holding element (24) sealingly fitting the opening of said housing (19) and defining with the wall thereof a chamber wherein said flange (1a) of the cell (1) can be limitedly displaced when said cell is moved apart from the bottom of its housing (19), and wherein said holding element (24) comprises a flange (30) sealingly fitting (29, 25, 35) said sliding cover plate (2) of said measuring cell (1).

9. A device according to claim 7, comprising means (11, 12, 14, 15) cooperating with the cell (1) for maintaining said sliding cover plate (2) in spaced relationship with the bottom of said cell (1), so that vacuum can be created therein.

10. A device according to claim 8, comprising means (11, 12, 14, 15) cooperating with the cell (1) for maintaining said sliding cover plate (2) in spaced relationship with the bottom of said cell (1), so that vacuum can be created therein.

* * * * *